(12) United States Patent
Fergusson et al.

(10) Patent No.: US 6,627,046 B1
(45) Date of Patent: Sep. 30, 2003

(54) SEPARATION OF THE PRODUCTS OF POLYAMIDE AMMONOLYSIS

(75) Inventors: Stuart Borden Fergusson, Kingston (CA); Yuhua Yan, Vernon Hills, IL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/489,214

(22) Filed: Jan. 21, 2000

(51) Int. Cl.[7] .................... B01D 3/14; C07C 209/86; C08J 11/04
(52) U.S. Cl. .................. 203/29; 203/74; 203/77; 203/DIG. 6; 203/99; 203/DIG. 19; 564/488; 521/49.8
(58) Field of Search .............. 203/29, 2, 99, 203/73, DIG. 19, 74, DIG. 6, 75, 77, 78; 528/310; 564/488; 521/49.8; 558/311; 562/593

(56) References Cited

U.S. PATENT DOCUMENTS

| | | | | |
|---|---|---|---|---|
| 3,900,450 A | * | 8/1975 | Jaswal et al. | 528/313 |
| 3,939,153 A | | 2/1976 | Fowler | |
| 3,950,229 A | * | 4/1976 | Moore et al. | 203/38 |
| 4,568,736 A | * | 2/1986 | Curatolo et al. | 528/310 |
| 5,109,104 A | * | 4/1992 | Marks | 528/313 |
| 5,302,756 A | | 4/1994 | McKinney | 564/488 |
| 5,395,974 A | | 3/1995 | McKinney | 564/488 |
| 5,441,607 A | | 8/1995 | Fuchs et al. | 203/49 |
| 5,495,016 A | | 2/1996 | Achhammer et al. | 540/539 |
| 5,874,575 A | * | 2/1999 | Fuchs et al. | 203/73 |
| 6,358,373 B1 | * | 3/2002 | Leemann et al. | 203/29 |

FOREIGN PATENT DOCUMENTS

| | | | |
|---|---|---|---|
| SU | 1373408 | 2/1988 | B01D/3/32 |
| WO | WO 9614291 | 5/1996 | |
| WO | WO 9723454 | 7/1997 | |

OTHER PUBLICATIONS

Malone et al., *Simple, Analytical Criteria for the Sequencing of Distillation Column*, AIChE Journal., vpl. 31, No. 4, pp. 683–689, Apr. 1985.

* cited by examiner

*Primary Examiner*—Virginia Manoharan (57) ABSTRACT

The useful reaction products in an output stream from an ammonolysis reactor are separated in a manner which minimizes the time during which high boiling polyamide intermediate material(s) are in contact with the amine-functional monomer product(s) or with the reactive monomer products in the stream.

20 Claims, 4 Drawing Sheets

SEPARATION OF THE PRODUCTS OF POLYAMIDE AMMONOLYSIS

BACKGROUND OF THE INVENTION

1. Field of the Invention

The present invention relates to the recycling of polyamide material, and in particular, to the separation of the useful reaction products of the ammonolysis of polyamide material.

2. Description of the Prior Art

It has long been considered ecologically desirable to reclaim polyamide material from used products, such as carpets, and to incorporate such reclaimed polyamide material into articles requiring high quality polymer. U.S. Pat. No. 5,302,756 and U.S. Pat. No. 5,395,974, both to McKinney and both assigned to the assignee of the present invention, relate to the ammonolysis of polyamide material into its constituent monomers.

Figure 1:
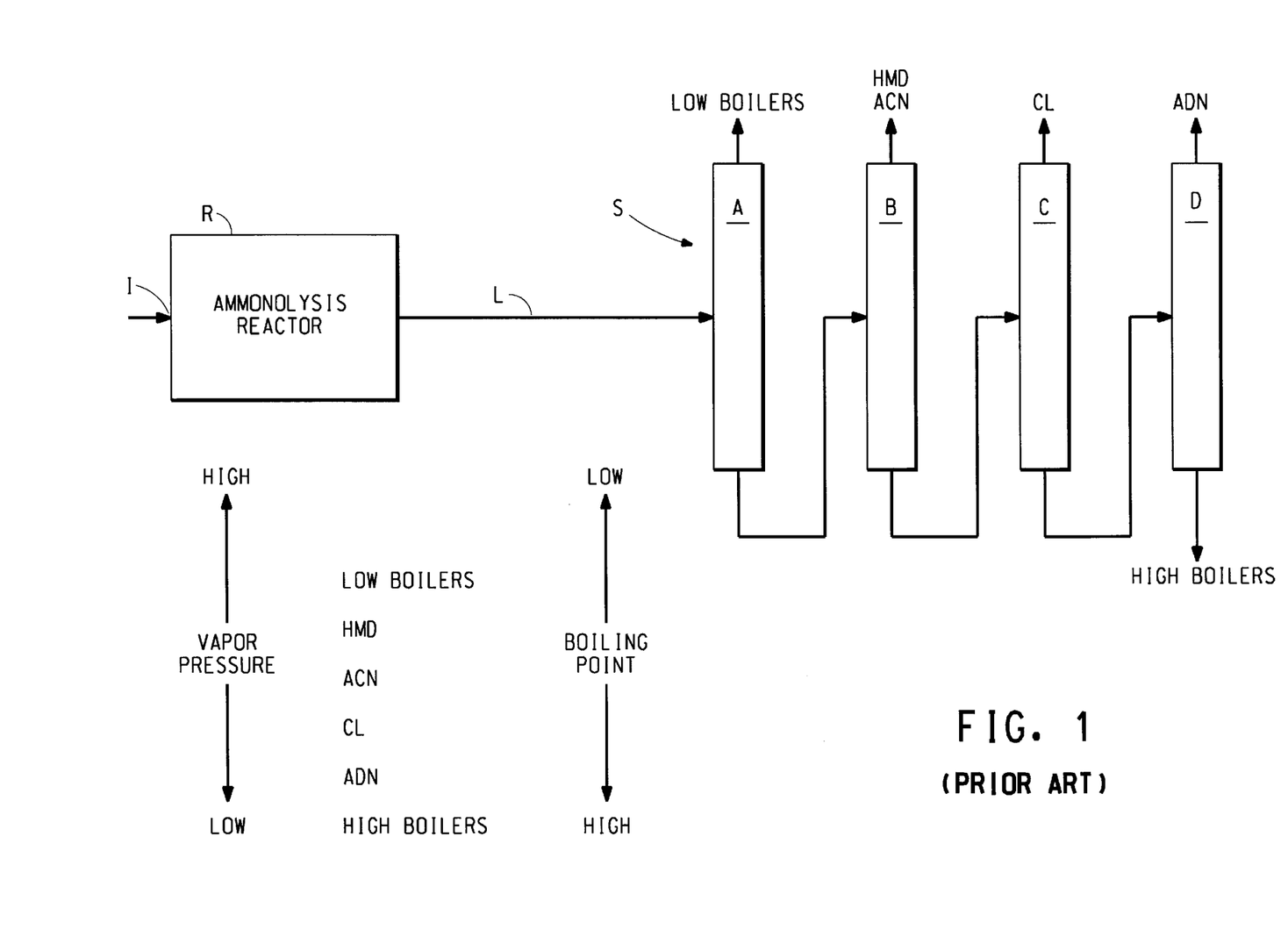
FIG. 1 is a schematic diagram of a distillation system in accordance with the teachings of the prior art for separating into fractions an output liquid stream from an ammonolysis reactor.

FIG. 1 is a schematic diagram in which an ammonolysis reactor R in accordance with the above-mentioned patents is connected by a line L to a distillation system S. The distillation system S is configured in accordance with the teachings of the prior art for separating into fractions the output liquid stream from the ammonolysis reactor R.

In the method described in the referenced McKinney patents polyamide material in the form of nylon 6, nylon 6,6, or a mixture thereof, is charged into the inlet port I of the reactor R. Within the reactor R the polyamide material is reacted with at least one equivalent of ammonia per amide group at temperatures in the range between two hundred fifty and four hundred seventy degrees Celsius (250 to 470° C.) and a pressure of at least one hundred (100) psig. The reaction is preferably carried out in the presence of certain Lewis Acid catalyst precursors.

The output from the ammonolysis reactor R, typically in liquid form, is conveyed by the line L to the distillation system S. The stream of ammonolysis products is a mixture of various useful reaction products as well as other, volatile, materials. These useful reaction products include:

(I) monomer product(s) having amine functionality, hereinafter referred to in this description as "amine-functional monomer product(s)". These amine-functional monomer product(s) have first, relatively high, predetermined vapor pressure(s) associated therewith;

(II) reactive polyamide material(s), hereinafter referred to in this description as "high boiling polyamide intermediate material(s)", or "high boilers" having second, relatively lower, predetermined vapor pressure(s) associated therewith; and (III) reactive monomer product(s) having vapor pressure (s) intermediate the first and second predetermined vapor pressures. These materials are hereinafter referred to in this description as "reactive monomer product(s)".

The other, volatile, materials include compounds, such as ammonia, water and carbon dioxide, having vapor pressures greater that the first-predetermined vapor pressure(s). These materials are hereinafter referred to in this description as "low boiling volatile product(s)" or "low boiler(s)" ("LB").

These reaction products and volatile materials contained in the output stream from the reactor R are listed in FIG. 1 in descending order of vapor pressures and in ascending order of boiling points.

The identity and relative quantity of the products output in the output line L is dependent upon the polyamide materials introduced into the ammonolysis reactor R.

If nylon 6,6 is charged into the ammonolysis reactor R the amine-functional monomer product in the output stream is hexamethylene diamine ("HMD") and the reactive monomer product is adiponitrile ("AND"). If nylon 6 is charged into the reactor R then the output stream contains a second, different, amine-functional monomer product, 6-aminocapronitrile ("ACN"), and a second, different, reactive monomer product, caprolactam ("CL"). Of course, if a mixture of both nylon 6,6 and nylon 6 is charged into the reactor R, then the output stream includes the amine-functional monomer product and the reactive monomer product generated by each type of nylon.

Amine-functional monomer products have a predetermined vapor pressure generally lying in the range from about twenty millimeters Mercury at one hundred twenty degrees Celsius (20 mm Hg @ 120° C.) to about eighty millimeters Mercury at the same temperature (80 mm Hg @ 120° C.). The vapor pressure of hexamethylene diamine is on the order of about eighty millimeters Mercury at one hundred twenty degrees Celsius (80 mm Hg @ 120° C.), while the vapor pressure of 6-aminocapronitrile is on the order of about twenty one millimeters Mercury at the same temperature (21 mm Hg @ 120° C.).

The high boiling polyamide intermediate material(s), which include polyamide intermediates, primary amides and nylon dimers and oligomers, have vapor pressures lower than the vapor pressure of the amine-functional monomer products, generally lower than two millimeters Mercury at one hundred twenty degrees Celsius (2 mm Hg@ 120C.).

Generally speaking, the vapor pressures of reactive monomer products are intermediate the vapor pressures of the high boiling polyamide intermediate material(s) and the amine-functional monomer products. That is to say, the reactive monomer product(s) have a vapor pressure lower than the vapor pressure(s) of the amine-functional monomer product(s) and higher than the vapor pressures of the high boiling polyamide intermediate material(s). For example, the vapor pressure of adiponitrile is on the order of 2.4 millimeters Mercury at one hundred twenty degrees Celsius (2.4 mm Hg @ 120° C.). The vapor pressure of caprolactam is on the order of six millimeters Mercury at the same temperature (6 mm Hg @ 120° C.).

These various output products from the ammonolysis reactor R must be separated from each other in order for them to be purified to the degree-necessary to permit their re-use. Distillation is a traditional mode of separation of commingled materials based upon their relative vapor pressures. Illustrated in FIG. 1 is a distillation system S based upon traditional prior art distillation teachings, such as those set forth by Malone et al., "Simple, Analytical Criteria for the Sequencing of Distillation Columns", AIChE Journal, April 1985, 683.

As a general rule, the basic heuristic observed for sequencing distillation columns is to remove the lightest components first. The distillation system S shown in FIG. 1 implements this heuristic. The system S is a four-pass system configured from four cascaded distillation columns A through D, respectively. These distillation columns A through D separate the ammonolysis products in a sequential order corresponding to their vapor pressures.

In operation, the commingled ammonolysis products in the output line L are fed into the first column A where the low boiling impurities are removed as distillate. The tails, or bottoms, stream from the first column A is fed into the second column B to remove as distillate the amine-functional monomer product(s), hexamethylene diamine and/or 6-aminocapronitrile, as the case may be. The reactive monomer product(s), such as caprolactam and/or adiponitrile, as the case may be, are removed as the distillates from the third and fourth columns C and D, respectively. The high-boiling polyamide intermediate materials ("HB") in the tails stream from the fourth column D contain amides, dimers, oligomers and tars. As used herein both the term "tails" and the term "bottoms" refer to the stream taken from the bottom of a given distillation column.

EXAMPLE 1

Comparative Example

The quantitative results of the operation of a four-column distillation system S as illustrated and described in connection with FIG. 1 is here set forth as a Comparative Example. It should be noted that the distillation columns A through D as shown in FIG. 1 were run as individual experiments and not as a continuous process.

The same column was used for all four separations. The column was two (2) inches in diameter and packed with five (5) feet of 0.16 inch metal protruded packing. The feed point was located two (2) feet from the bottom of the packed column in the first two columns, and just above the reboiler in the last two columns. The reboiler was a twenty-two (22) liter pot heated by an electric heating mantle.

The operating parameters for the column when emulating the operation of each of columns A through D of FIG. 1 were as follows:

|  |  | A | B | C | D |
|---|---|---|---|---|---|
| Feed line temperature | ° C. | r.t. | r.t. | 60 | 100 |
| Preheater temperature | ° C. | 40 | 100 | 130 | 140 |
| Feed flow rate | Kg/h | 4.0 | 2.0 | 1.0 | 2.0 |
| Differential Pressure | Torr | 1.5 | 25 | ~30 | ~25 |
| Condenser water temperature | ° C. | ~10 | ~10 | 75 | 75 |
| Head vacuum | Torr | 300 | 20 | 20 | 20 |
| Head temperature | ° C. | 73 | ~110 | ~154 | ~176 |
| Reflux ratio |  | 0 | 0.4 | 2.0 | 0 |
| Residence time in reboiler | h | 0.5 | 1 | 2 | 1 |
| Reboiler temperature | ° C. | 197 | 192 | 222 | 291 |
| Distillate line temperature | ° C. | — | — | 75 | 75 |
| Tails line temperature | ° C. | — | — | 100 | ~150 | r.t. = room temperature

Although the distillation columns were run as individual experiments and not run as continuous process an overall recovery of distillation system S as configured in FIG. 1 can be calculated by multiplying the recoveries in each step for each individual monomer.

The recovery of each monomer was calculated as follows:

For a monomer in the distillate:

$$\% \text{ Recovery of Monomer} = \frac{(\text{flow rate of Monomer in distillate} + \text{flow rate of Monomer in cold traps}) \times 100}{(\text{flow rate of Monomer in feed})}$$

For a monomer in the tails stream:

$$\% \text{ Recovery of Monomer} = \frac{(\text{flow rate of Monomer in tails stream}) \times 100}{(\text{flow rate of Monomer in feed})}$$

The % Loss or Gain of each monomer was calculated as follows:

$$\% \text{ Loss or gain of Monomer} = \frac{(\text{flow rate of Monomer in distillate, tails, cold traps} - \text{flow rate of Monomer in feed}) \times 100}{(\text{flow rate of Monomer in feed})}$$

The overall recovery of the four monomers, viz., hexamethylene diamine, 6-aminocapronitrile, adiponitrile and caprolactam, in this example was sixty-seven percent (67%).

The results are summarized in the following Table 1.

TABLE 1

| | | Composition % | | | | |
|---|---|---|---|---|---|---|
| | Feed | Distillate Column A | Distillate Column B | Distillate Column C | Distillate Column D | Tails Column D |
| HMD | 12 | 0.049 | 48 | 1.4 | 0.7 | 0.036 |
| ACN | 15 | 0.095 | 46 | 10 | 6 | 0.044 |
| CL | 18 | 0.089 | 0.053 | 85 | 11 | 0.078 |
| ADN | 24 | 0.018 | 0.021 | 0.5 | 55 | 1.9 |

| | Overall Recovery % | Recovery % | | | |
|---|---|---|---|---|---|
| | | Column A | Column B | Column C | Column D |
| HMD | 64 | 70.5 | 90.4 | | |
| ACN | 72 | 87.6 | 82.7 | | |
| CL | 52 | 88.3 | 65.8 | 89.4 | |

TABLE 1-continued

| | | | | | |
|---|---|---|---|---|---|
| ADN | 22 | 103.5 | 78.5 | 54.7 | 48.8 |
| | Overall Reaction and Physical Gain/Loss, | | Reaction and Physical Gain/Loss, % of feed | | |
| | % of feed | Column A | Column B | Column C | Column D |
| HMD | Lost 17 | Lost 29 | Lost 8 | | |
| ACN | Lost 17 | Lost 12 | Lost 14 | | |
| CL | Lost 1 | Lost 12 | Lost 3 | Lost 6 | |
| ADN | Lost 60 | Gain 4 | Lost 21 | Lost 42 | Lost 47 |

The low recoveries from the four-column prior art distillation system S of FIG. 1 is believed to be due to the reactive nature of the ammonolysis products. Reactions between the amine-functional monomer product(s) and the primary amides in the high boiling polyamide intermediate materials limit the recovery rates for hexamethylene diamine and 6-aminocapronitrile. In addition, the amine functionality in the high boiling polyamide intermediate materials catalyzes the thermal degradation of adiponitrile, which limits the recovery of this reactive monomer product.

In view of the foregoing, it is believed advantageous to have a more efficient separation process in which reactions among the various ammonolysis products are reduced, with a concomitant increase in the recovery of the desirable monomer products.

SUMMARY OF THE INVENTION

The present invention is directed toward a process for separating into fractions an output stream from an ammonolysis reactor. The output stream includes the useful reaction products:

(I) amine-functional monomer product(s);

(II) high boiling polyamide intermediate material(s);

(III) reactive monomer product(s).

The output stream also may include:

(IV) low boiling volatile product(s).

The present invention is based upon the recognition that it is the prolonged presence of the high boiling polyamide intermediate material(s) in the distillation system in contact with the amine-functional monomer product(s) or with the reactive monomer products that limits the recovery rates of these useful monomer products.

Therefore, in accordance with a first embodiment of the present invention, as the first treatment of the output stream that separates at least one of these useful reaction products from the other reaction products, the high boiling polyamide intermediate material(s) are separated from both the amine-functional monomer product(s) and the reactive monomer product(s).

In accordance with a first implementation of the first embodiment of the invention the amine-functional monomer product(s) and the reactive monomer product(s) are taken as a distillate stream from a first distillation column. The high boiling polyamide intermediate material(s) separate in the tails from the first distillation column.

In an alternate implementation of the first embodiment of the invention, as the first treatment of the output stream from the ammonolysis reactor that separates at least one of the useful reaction products from the others, the amine-functional monomer product(s) are separated as the distillate stream from a first distillation column, while the reactive monomer product(s) are taken as a side draw from the column. The high boiling polyamide intermediate material(s) again separate in the tails from the distillation column.

Depending upon the polyamide material charged into the ammonolysis reactor the amine functional monomer product(s) may be hexamethylene diamine and/or 6-aminocapronitrile, while the reactive monomer product(s) may be adiponitrile and/or caprolactam. In more particularized versions of either implementation of the first embodiment of the invention, additional distillation columns are provided to separate the plural amine functional monomer product(s) from each other and to separate the plural reactive monomer product(s) from each other.

In accordance with a second embodiment of the present invention, as the first treatment of the output stream that separates at least one of these useful reaction products from the other reaction products, the high boiling polyamide intermediate material(s) together with the reactive monomer product(s) are separated from the amine-functional monomer product(s). As an immediately following second step, the reactive monomer product(s) are separated from the high boiling polyamide intermediate material(s).

BRIEF DESCRIPTION OF THE DRAWINGS

The invention will be more fully understood from the following detailed description thereof, taken in connection with the accompanying drawings, which form a part of this application, and in which.

DETAILED DESCRIPTION OF THE INVENTION

Throughout the following detailed description similar reference numerals refer to similar elements in all Figures of the drawings.

First Embodiment

Figure 2:
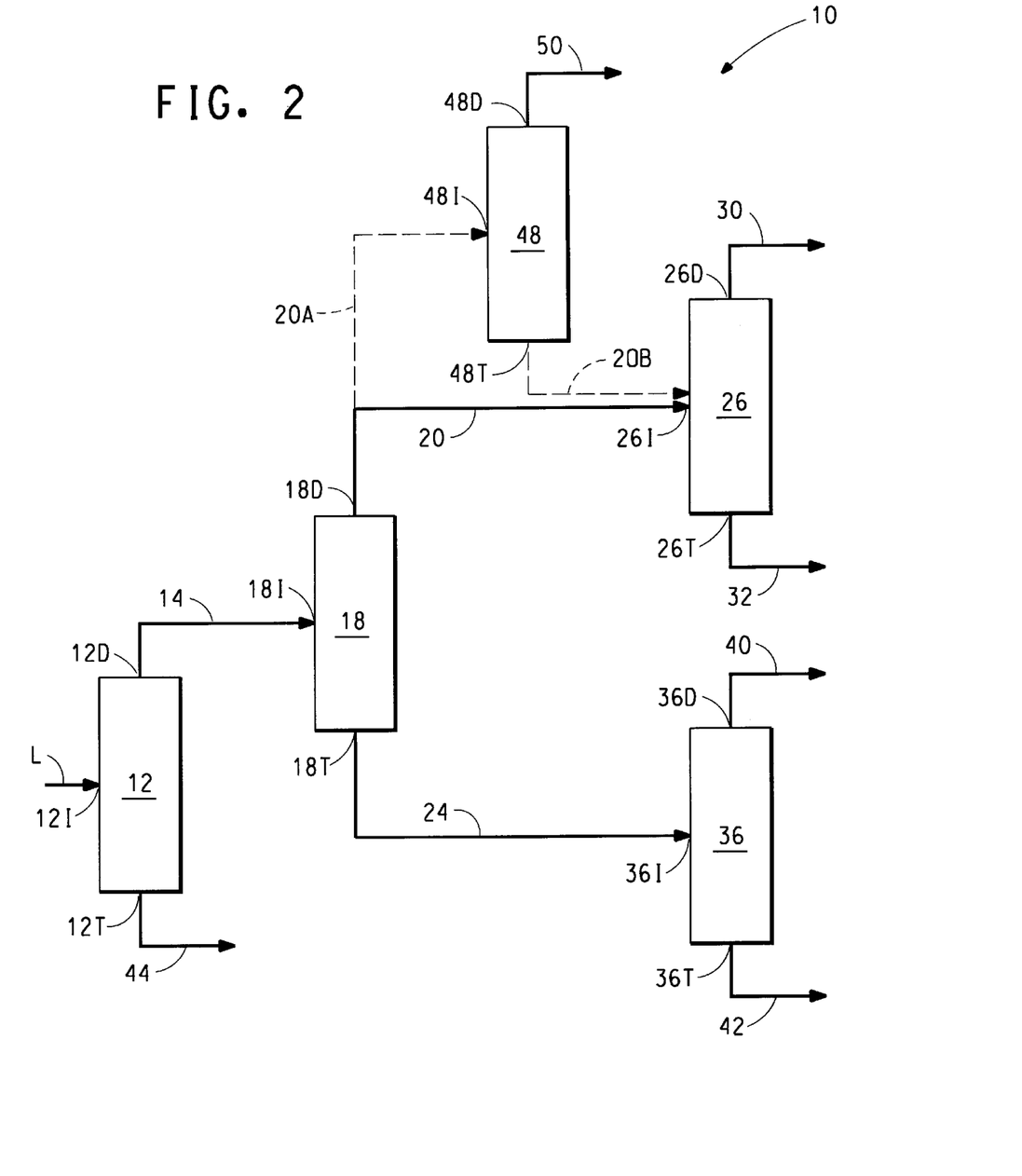
FIG. 2 is a schematic diagram of a distillation system for practicing the separation process in accordance with a first implementation of the first embodiment of the present invention.

With reference to FIG. 2 shown is a schematic diagram of a distillation system 10 for practicing the separation process in accordance with a first embodiment of the present invention. The distillation system 10 implemented in FIG. 2 includes a first distillation column 12 that is connected at its input port 12I to the output line L from the ammonolysis reactor R. The output stream from the ammonolysis reactor R carried by the line L includes the following useful reaction products:

(I) amine-functional monomer product(s) having a first predetermined vapor pressure associated therewith;

(II) high boiling polyamide intermediate material(s) having a vapor pressure lower than the first predetermined vapor pressure; and (III) reactive monomer product(s) having an intermediate vapor pressure between the lower vapor pressure and the first vapor pressure.

The output stream in the line L also may include:

(IV) low boiling volatile product(s).

The distillate output port 12D from the column 12 is connected over a line 14 to the input port 18I of a distillation column 18. A line 20 is connected to the distillate output port 18D of the column 18, while the tails output port 18T from the column 18 is connected to a line 24.

The line 20 is connected to the input port 26I of a distillation column 26. The distillate output port 26D and the tails output port 26T of the distillation column 26 are connected to lines 30, 32, respectively.

The line 24 is connected to the input port 36I of a distillation column 36. The distillate output port 36D and the tails output port 36T of the distillation column 36 are connected to lines 40, 42, respectively.

The tails output port 12T from the column 12 is connected to a line 44.

Preferably, the columns 12, 18, 26 and 36 are each implemented using distillation column technology familiar to those practiced in the art. The interior of the columns may be either trays or packings having sufficient stages to achieve the required separations. The columns must be run under vacuum to minimize the temperature of the ammonolysis products. Each of the columns 12, 18, 26 and 36 has a respective low residence reboiler therein.

Having set forth the configuration of the distillation system 10 its operation when practicing a first implementation of the first embodiment of the process of the present invention may now be discussed.

As noted earlier the identity of the particular amine-functional monomer product(s) and of the intermediate vapor pressure reactive monomer product(s) in the line L depends upon the particular polyamide material(s) charged into the ammonolysis reactor R. If only nylon 6,6 is charged into the ammonolysis reactor R the amine-functional monomer product in the stream in the output line L is hexamethylene diamine and the intermediate vapor pressure reactive monomer product is adiponitrile. If only nylon 6 is charged into the reactor R then the amine-functional monomer product in the output stream is 6-aminocapronitrile and the intermediate vapor pressure reactive monomer product is caprolactam. If a mixture of both nylon 6,6 and nylon 6 is charged into the reactor R, then the output stream includes the amine-functional monomer product and the intermediate vapor pressure reactive monomer product generated by each type of nylon. During the discussion of the operation of both embodiments of the present invention it is assumed that both nylon 6,6 and nylon 6 are charged into the reactor R.

The underlying premise of the present invention is to separate the high boiling polyamide intermediate material(s) from both the amine-functional monomer product(s) and from the intermediate vapor pressure reactive monomer products as early as possible in the course of distillation in the system 10.

Therefore, in accordance with the basic premise of the system 10, the distillation column 12 separates the amine-functional monomer products together with the intermediate vapor pressure reactive monomer products from the high boiling polyamide intermediate material(s). This separation is the first treatment of the output stream from the reactor R that separates at least one of the useful reaction products from the others.

The amine-functional monomer product together with the intermediate vapor pressure reactive monomer products emerge in the distillate stream from the port 12D of the column 12 carried by the line 14. The high boiling polyamide intermediate material(s) is taken as a tails stream from the port 12T of the distillation column 12.

The distillate stream in the 14 from the first distillation column 12 is conveyed to the distillation column 18. The distillate fraction emanating at the port 18D of the column 18 contains the amine-functional monomer product(s). The tails fraction emanating at the port 18T of the column 18 contains the intermediate vapor pressure reactive monomer product(s).

Since it is assumed that both nylon 6,6 and nylon 6 are charged into the reactor R, two different amine-functional monomer products are present in the distillate carried by the line 20. These different amine-functional monomer products may be separated from each other. The amine-functional monomer products are conveyed by the line 20 to the distillation column 26. The column 20 separates one of the amine-functional monomer products (e.g., the amine-functional monomer product hexamethylene diamine generated from nylon 6,6) as the distillate fraction carried on the line 30. The second amine-functional monomer product (e.g., the amine-functional monomer product 6-aminocapronitrile generated from nylon 6) separates as the tails fraction from the column 26 on the line 32. The fractions on the lines 30, 32 are conveyed for further processing, if desired.

Again, since both nylon 6,6 and nylon 6 are assumed to be present in the reactor R, two different intermediate vapor pressure reactive monomer products are present in the tails stream carried from the column 18 by the line 24. These different intermediate vapor pressure reactive monomer products may also be separated from each other. The intermediate vapor pressure reactive monomer product(s) are conveyed by the line 24 to the distillation column 36. In the column 36 one of the reactive monomer products (e.g., the intermediate vapor pressure reactive monomer product caprolactam generated from nylon 6) is separated as the distillate fraction carried on the line 40. The other intermediate vapor pressure reactive monomer product (e.g., the intermediate vapor pressure reactive monomer product adiponitrile generated from nylon 6,6) separates as the tails fraction from the column 36 on the line 42. The fractions on the lines 40, 42 are conveyed for suitable further processing, as desired.

It should be noted that if only a single form of nylon is charged into the reactor R the separation performed by the column 26 would not be necessary, and the amine-functional monomer product in the distillate carried by the line 20 is carried directly to further processing. Similarly, if only a single form of nylon is charged into the reactor R the separation performed by the column 36 would also not be necessary.

As alluded to earlier the output stream from the reactor R may also include low boiling volatile product(s) such as ammonia, water and carbon dioxide. The low boiling volatile product(s) have vapor pressure(s) higher than the first predetermined vapor pressure. These low boiling volatile product(s) may be preliminarily removed from the line L by a column similar to the column A in the prior art system S (FIG. 1) disposed in the line L upstream of the column 12.

If the low boiling volatile product(s) are not preliminarily removed such products enter the distillation system 10 together with the useful reaction products. In the implementation of the process of the present invention embodied by the distillation system 10 the low boiling volatile product(s) separate with the amine-functional monomer product(s) in the distillate fractions from both the first distillation column 12 on the line 14 and from the distillation column 18 on the line 20. To remove the low boiling volatile product(s) an additional column 48 is connected between the distillate port 18D of the column 18 and the input port of the column 26. In this event the line 20 is interrupted and the distillate fraction from the port 18D is carried over a line 20A to the input port 48I of the column 48. The low boiling volatile product(s) separate from the distillate port 48D of the column 48 over a line 50, while the tails fraction at the port 48T [containing the amine-functional monomer product(s)] is conveyed either to the column 26 over the line 20B (if plural amine-functional monomer products are present) or directly for further processing (if only a single amine-functional monomer product is present).

As noted, the first distillation column 12 and the distillation column 36 may each have a reboiler respectively associated therewith. The residence of the tails in the reboiler of the first distillation column 12 is less than one hour. The residence of the reactive monomer adiponitrile in the reboiler of the distillation column 36 is less than two hours.

Figure 3:
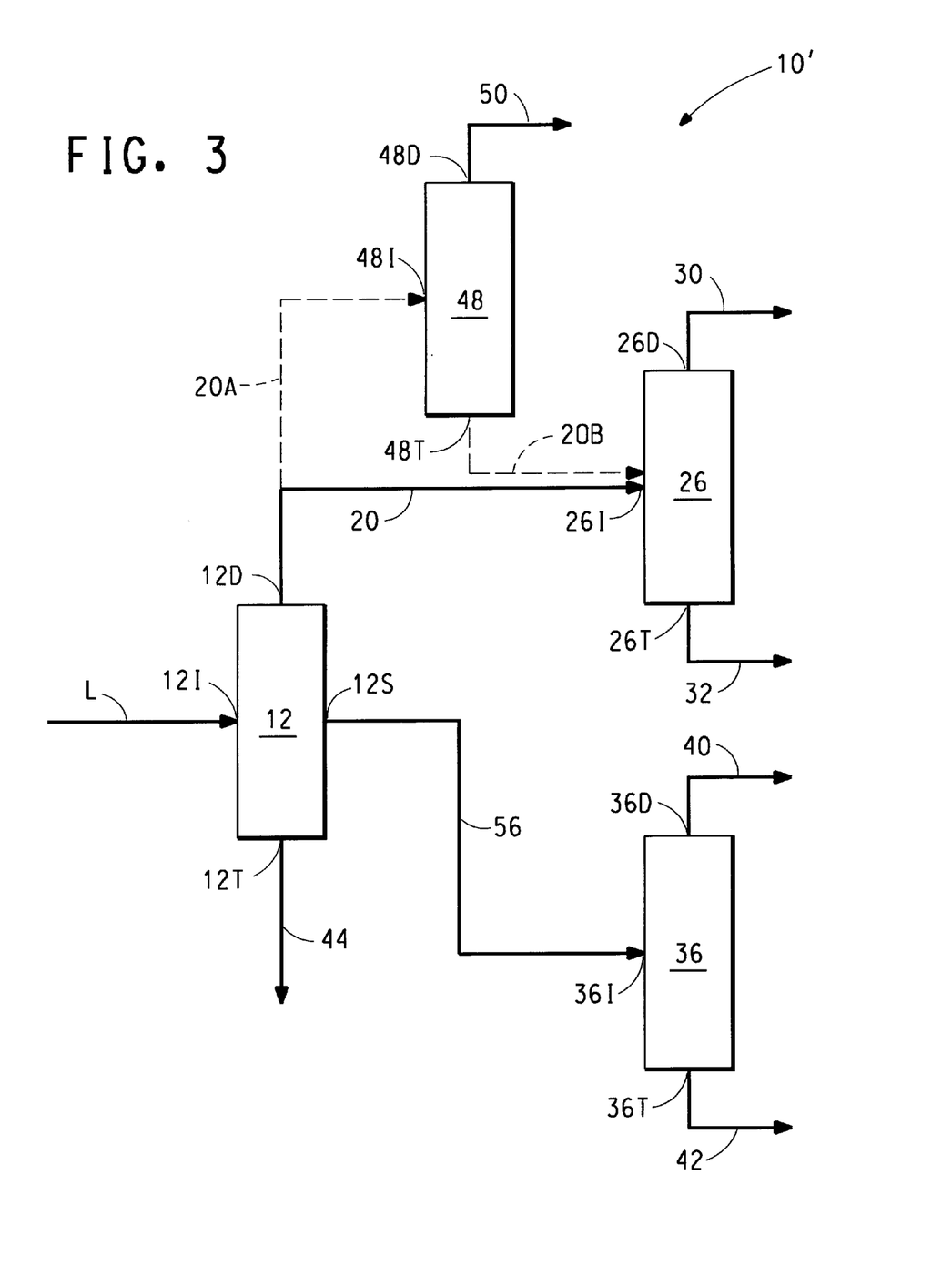
FIG. 3 is a schematic diagram of a distillation system for practicing the separation process in accordance with an alternate implementation of the first embodiment of the present invention.

FIG. 3 illustrates a schematic diagram of an alternative implementation of the distillation system, indicated by the reference character 10', for practicing the separation process in accordance with first embodiment of the present invention. In the modification shown in FIG. 3 the high boiling polyamide intermediate material(s) are again separated from both the amine-functional monomer product(s) and from the intermediate vapor pressure reactive monomer products as the first treatment of the output stream from the reactor R that separates at least one of the useful reaction products from the others.

However, in the distillation in the system 10' the intermediate vapor pressure reactive monomer product(s) are taken as a side draw stream from a port 12S in the first distillation column 12. The intermediate vapor pressure reactive monomer product(s) are carried over a line 56. The line 56 may be connected to the input port 36I of the distillation column 36 if plural intermediate vapor pressure reactive monomer product(s) are present. Otherwise, the product on the line 56 may be taken directly for further processing.

The amine-functional monomer product(s) and are carried over the line 20 connected to the distillate port 12D of the column 12. If plural amine-functional monomer product(s) are present the line 20 is connected to the input port 26I of the column 26. In the column 26 the plural amine-functional monomer product(s) are separated from each other. If only a single amine-functional monomer product is present, the line 20 may be connected directly to a suitable location for appropriate further processing.

Low boiling volatile product(s) are treated analogously to the treatment described in connection with the system 10 of FIG. 2. If not preliminarily removed, such products enter the distillation system 10' and separate with the amine-functional monomer product(s) in the distillate fraction from the first distillation column 12. To remove the low boiling volatile product(s) the additional column 48 is connected between the distillate port 12D of the column 12 and the input port 26I of the column 26. The distillate fraction from the port 12D is carried over the line 20A to the input port 48I of the column 48. The low boiling volatile product(s) separate from the distillate port 48D of the column 48 over a line so, while the tails fraction at the port 48T [containing the amine-functional monomer product(s)] is conveyed either to the column 26 over the line 20B (if plural amine-functional monomer products are present) or directly for further processing (if only a single amine-functional monomer product is present).

Each of the columns illustrated in FIG. 3 has a low residence reboiler therein.

Second Embodiment

Figure 4:
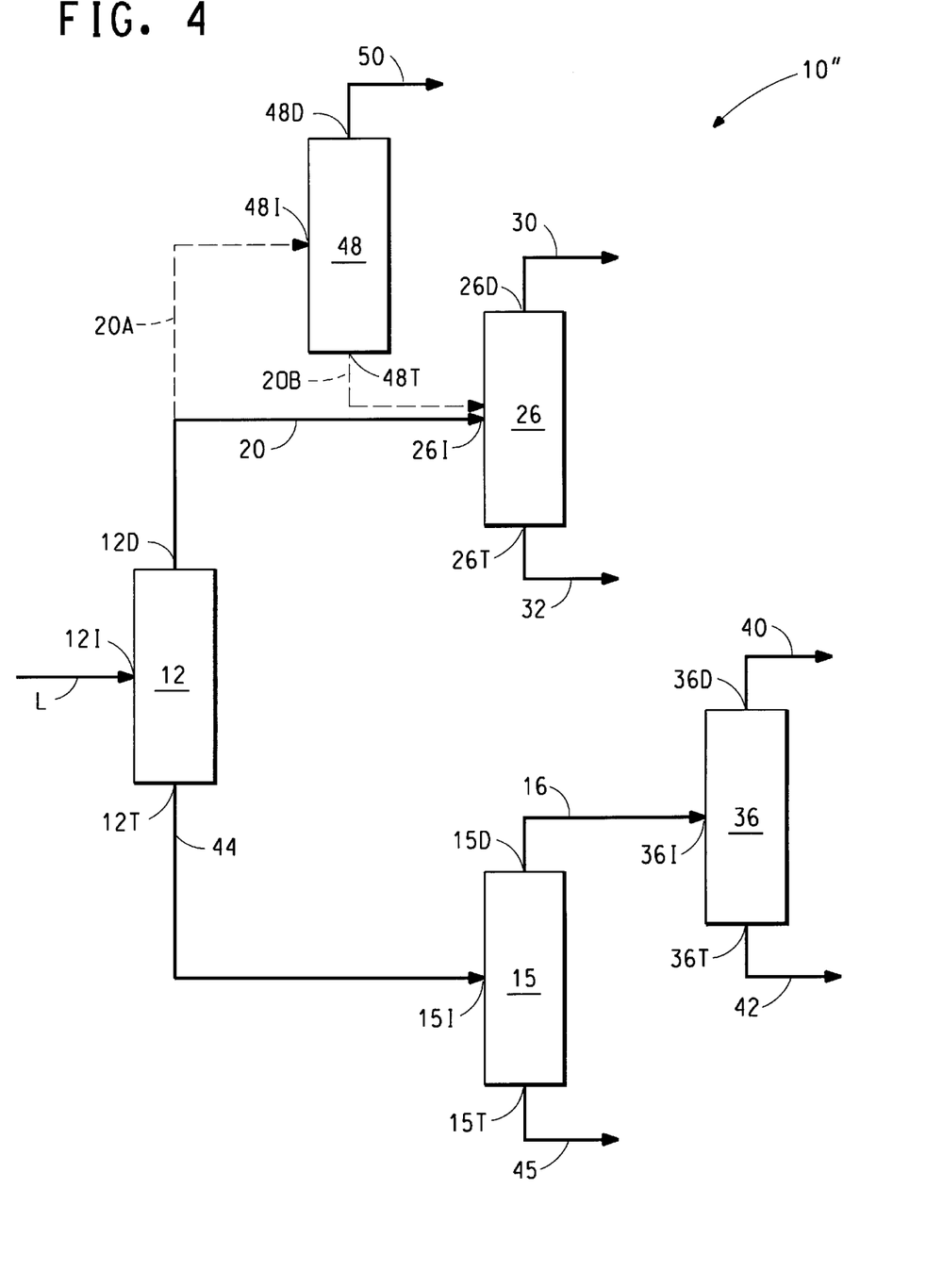
FIG. 4 is a schematic diagram of a distillation system for practicing the separation process in accordance with a second embodiment of the present invention.

FIG. 4 illustrates a schematic diagram of a distillation system 10" for practicing the separation process in accordance with a second embodiment of the present invention.

In the modification shown in FIG. 4, as the first treatment of the output stream that separates at least one of the useful reaction products from the others, a first distillation column 12 is used to separate the monomer having the amine functionality from the reactive monomer having the intermediate vapor pressure and the high boiling polyamide intermediate material. The monomer having the amine functionality is taken as the distillate fraction from the column 12 on the line 20. The intermediate vapor pressure reactive monomer(s) and the high boiling polyamide intermediate material are taken as the tails fraction from the column 12 on the line 44.

The line 44 from the column 12 is connected to a distillation column 15 located immediately downstream of the first column 12. In the distillation column 15 the intermediate vapor pressure reactive monomer(s) are immediately separated from the high boiling polyamide intermediate material. The intermediate vapor pressure reactive monomer(s) are taken as the distillate fraction from the distillate outlet port 15D of the column 15 while the high boiling polyamide intermediate material is taken as the tails fraction from the tails outlet port 15T. The tails outlet port 15T is connected to a line 45. If plural intermediate vapor pressure reactive monomers are present, they are conveyed over the line 16 to the distillation column 36 for separation.

The system 10" in accordance with the second embodiment still implements the underlying premise of the present invention in that the high boiling polyamide intermediate material(s) are separated from the amine-functional monomer product(s) and from the intermediate vapor pressure reactive monomer products as early as possible in the course of distillation in the system 10.

If plural amine functional monomers are present in the distillate fraction of column 12, the line 20 is connected to the column 26. In the column 26 the first amine monomer, e.g., hexamethylene diamine, is separated as the distillate fraction on the line 30 from the second amine monomer e.g., 6-aminocapro-nitrile, on the line 32.

Low boiling volatile product(s) are treated analogously to the treatment described in connection with the system 10 of FIG. 2. If not preliminarily removed such products enter the distillation system 10" and separate with the amine-functional monomer product(s) in the distillate fraction from the first distillation column 12. The distillate fraction from the port 12D is carried over the line 20A to the input port 48I of the column 48. The low boiling volatile product(s)

separate from the distillate port 48D of the column 48 over the line 50, while the tails fraction [containing the amine-functional monomer product(s)] is conveyed either to the column 26 over the line 20B (if plural amine-functional monomer products are present) or directly for further processing (if only a single amine-functional monomer product is present).

Each of the columns illustrated in FIG. 4 has a low residence reboiler therein. The residence of the tails from the first distillation column 12 is less than one hour. The residence of the reactive monomer adiponitrile in the reboiler 36R of the distillation column 36 is less than two hours.

EXAMPLES

The quantitative results of the operation of the various embodiments of the present invention as illustrated and described in connection with FIGS. 2 through 4 are set forth in the following Examples. Similar to the situation in connection with Comparative Example 1, the distillation columns shown in FIGS. 2 through 4 were each implemented as an individual experiment and not as a continuous process.

A summary of key process variables for Examples 2 through 4 is presented in the following table.

example caprolactam was separated overhead and adiponitrile was taken as tails. The demonstrated steps result in high recoveries of these four ammonolysis reaction products.

Column 2.1 A distillation column, with a diameter of two inches, was packed with four (4) feet of 0.24 inch cross-section metal protruded packing material. The feed location was one (1) foot from the bottom of the packed column. On top of the column was a condenser which employed cooling water at seven degrees Celsius (7° C.). A head vacuum of twenty (20) torr was provided by a vacuum pump, and the resulting head temperature was one hundred thirty two degrees Celsius (132° C.). Two cold traps, one filled with ice and the other with dry ice, were placed just before the vacuum pump to condense any remaining vapor. The reflux ratio was 0.25.

An electrically heated reboiler including a flask and a heating mantle was located the bottom of the column. The liquid in the reboiler was varied from two hundred sixty degrees Celsius (260° C.) to two hundred ninety degrees Celsius (290° C.). The liquid level in the reboiler was monitored by measuring the differential pressure between the top and the bottom of the liquid. When a change in the liquid level from the set point was detected, a controller would instruct the opening or the closing of a valve below the reboiler to maintain a constant level. A gear pump was used to draw the tails stream from the reboiler to a receiver.

|  |  | (2.1) | (2.2) | (2.3) | (3.1) | (4.1) | (4.2) |
|---|---|---|---|---|---|---|---|
| Feed line temperature | ° C. | 80 | r.t. | 100 | r.t. | r.t. | 60 |
| Preheater temperature | ° C. | 80 | 60 | 140 | 122 | 122 | 130 |
| Feed flow rate | Kg/h | 1.0 | 4.0 | 2.0 | 1.3 | 1.3 | 1.0 |
| Differential Pressure | Torr | ~25 | 1.5 | ~25 | 13 | 15 | ~30 |
| Condenser water temperature | ° C. | 7 | ~10 | 75 | 8 | 8 | 75 |
| Head vacuum | Torr | 20 | 300 | 10 | 14 | 20 | 10 |
| Head temperature | ° C. | 132 | 73 | 131 | 101 | 105 | 140 |
| Reflux ratio |  | 0.25 | 0.6 | 1 | 0.4 | 0.4 | 0.2 |
| Residence time in reboiler | h | ~2 | 0.5 | 1 | 0.4 | 0.6 | 2 |
| Reboiler temperature | ° C. | 260–290 | 179 | 180.6 | 285 | 183 | 280 |
| Distillate line temperature | ° C. | — | — | 75 | — | — | 75 |
| Tails line temperature | ° C. | — | — | ~150 | — | 100 | 150 | r.t. = room temperature

The recovery of each individual useful reaction product and the overall recovery of distillation system were calculated in the same manner as in Example 1.

Example 2

This example illustrates the operation of a distillation column when configured to operate as the columns 12, 48 and 36 shown in FIG. 2. When configured to act as the first column 12, hexamethylene diamine, 6-aminocapronitrile, adiponitrile and caprolactam and the low boilers were taken overhead and the high boilers are removed as a tails stream. When configured to act as the distillation column 48 the low boilers were separated overhead while the hexamethylene diamine and 6-aminocapronitrile were taken as tails. When configured to act as the third distillation column 36 in this This column was operated as column 12 of FIG. 2. Ammonolysis product having seventeen percent (17%) hexamethylene diamine ("HMD"), twenty-one percent (21%) 6-aminocapronitrile ("ACN"), twenty-one percent (21%) caprolactam ("CL"), and nine percent (9%) adiponitrile ("AND"), and also high and low boiling impurities (high and low boilers) was kept stirred and blanketed in nitrogen in a feed tank under a pressure of seven to eight (7 to 8) psig. Before being drawn into the distillation column by pressure difference the feed stream passed through a ninety micrometer (90 μm) filter and then an electric preheater in which it was heated to eighty degrees Celsius (80° C.). The feed flow rate was controlled automatically with a flow control valve with the signal from a mass flowmeter at one kilogram per hour (1.0 kg/h).

The results are summarized in the Table 2–1.

TABLE 2-1

|     | Recovery, % of feed | Reaction and Physical loss/gain, % of feed | Composition % Feed | Composition % Distillate |
| --- | --- | --- | --- | --- |
| HMD | 94  | Lost 6 | 17  | 21  |
| ACN | 102 | Gain 2 | 21  | 28  |
| CL  | 98  | Lost 2 | 21  | 27  |
| ADN | 86  | Lost 14 | 9   | 10  |

Column 2.2 A distillation column similar to that described for the Column 2.1, except having packing with a height of three (3) feet, was operated as column 48 in FIG. 2. A distillate stream containing thirty-six percent (36%) hexamethylene diamine, forty-three percent (43%) 6-aminocapronitrile and impurities (mainly water) at sixty degrees Celsius (60° C.) was fed into this column. The feed location was again one (1) foot from the bottom of the packed column.

The reboiler was a three (3) liter pot (vented to the atmosphere) positioned inside a five (5) liter pot. The process liquid flowed into the clearance between the two pots where it was heated by an electric heating mantle located on the outside surface of the five liter pot. The design of a reboiler decreased the hold-up volume without reducing the heating surface area.

The results are summarized in the Table 2–2.

TABLE 2-2

|     | Recovery, % of feed | Reaction & Physical loss/gain, % of feed | Composition % Feed | Composition % Distillate | Composition % Tails |
| --- | --- | --- | --- | --- | --- |
| HMD | 100 | 0 | 36 | 0.071 | 42 |
| ACN | 101 | Gained 1 | 43 | 0.026 | 51 |
| water |  | Lost 2 | 15 | 95 | 0.270 |

Column 2.3 A distillation column similar to that described for the Column 2.1, except having packing with a height of three (3) feet, was operated as column 36 in FIG. 2. A stream containing sixty-one percent (61%) caprolactam and eighteen percent (18%) adiponitrile was fed into a feed location two (2) feet from the bottom of the packed column. The reboiler described above in the Column 2.2 was used.

The results are summarized in the Table 2–3.

TABLE 2-3

|     | Recovery, % of feed | Reaction and Physical loss/gain, % of feed | Composition % Feed | Composition % Distillate | Composition % Tails |
| --- | --- | --- | --- | --- | --- |
| CL  | 97  | −1  | 61  | 80  | 3.3 |
| ADN | 97  | 2   | 18  | 1.2 | 66  |

Example 3

This example illustrates the operation of a distillation column when configured to operate as the columns 12, 48 and 36 shown in FIG. 3. In the first column 12 hexamethylene diamine, 6-aminocapronitrile, and the low boilers were taken overhead. Adiponitrile and caprolactam were removed as side draw products, leaving the high boilers as a tails stream. The distillate from the first column was taken to the second column (48) where water and other low boilers were removed from hexamethylene diamine and 6-aminocapronitrile. Hexamethylene diamine was not removed from 6-aminocapronitrile in this example. The side draw from the first column (12) was taken to a third column (36) where adiponitrile (tails stream) was separated from caprolactam.

Column 3.1 A two (2) inch diameter column was packed with two (2) feet of 0.24 inch cross-section metal protruded packing material. This column was operated as column 12 in FIG. 3.

Ammonolysis product having of sixteen percent (16%) hexamethylene diamine ("HMD"), twenty-three percent (23%) 6-aminocapronitrile ("ACN"), eighteen percent (18%) caprolactam ("CL"), and eleven percent (11%) adiponitrile ("AND"), and also high and low boiling materials (high and low boilers) were fed into the distillation column 12 after passing through a ninety micrometer (90 μm) filter.

The vapor side-stream draw-off was located at one (1) foot from the bottom of the packed column. The side-draw stream passed through a condenser which employed water at seventy-five degrees Celsius (75° C.). All of the distillate from this side-draw condenser was collected in a receiver at a flow rate of 0.4 kg/h. To keep the caprolactam in liquid form, the side-draw product line was heated.

At the bottom of the column an electrically heated thermosiphon reboiler with a low hold-up volume of about four hundred (400) mL provided the necessary heat to the process. The low reboiler volume and the relatively high feed flow rate contributed to a low residence time of 0.4 hour for the reboiler content, thereby minimizing reaction losses of the monomers. The liquid in the reboiler was maintained at two hundred eighty-five degrees Celsius (285 ° C.).

The results are summarized in Table 3–1.

TABLE 3-1

|     | Recovery (% of feed) | Reaction & Physical loss/gain (% of feed) | Composition % Feed | Composition % Distillate | Composition % Side-draw | Composition % Tails |
| --- | --- | --- | --- | --- | --- | --- |
| HMD | 96 | Lost 3   | 16 | 35   | 0.62 | 0.000 |
| ACN | 97 | Gained 3 | 23 | 51   | 4.46 | 0.081 |
| CL  | 92 | Gained 1 | 18 | 3.79 | 53   | 0.309 |
| ADN | 98 | Gained 1 | 11 | 0.23 | 36   | 0.903 |

Column 3.2 This column was the same as Column 2.2 in Example 2.

Column 3.3 This column was the same as Column 2.3 in Example 2.

Example 4

This example illustrates the operation of a distillation column when respectively configured to operate as the columns 12, 15 and 36 shown in FIG. 4. In the first column 12 hexamethylene diamine, 6-aminocapronitrile, and the low boilers were taken overhead. Adiponitrile and caprolactam and the high boilers were taken as a tails stream. In the second column 15 adiponitrile ("AND") and caprolactam ("CL") were taken overhead leaving the high boilers in the tails stream. The distillate from the first column (15) was taken to a third column (36) where caprolactam was taken overhead and adiponitrile was taken in the tails stream.

Column 4.1 A distillation column, with a diameter of two inches, was packed with four (4) feet of 0.24 inch cross-section metal protruded packing material. The feed location was one foot from the bottom of the packed column. On top of the column was a condenser which employed cooling water at seven degrees Celsius (7° C.). A head vacuum of twenty (20) torr was provided by a vacuum pump, and the resulting head temperature was one hundred five degrees Celsius (105° C.). Two cold traps, one filled with ice and the other with dry ice, were placed just before the vacuum pump to condense any remaining vapor. The reflux ratio was one (1).

At the bottom of the column an electrically heated thermosiphon reboiler with a low hold-up volume of about four hundred milliliters (400 mL) provided the necessary heat to the process. The low reboiler volume and the relatively high feed flow rate contributed to a low residence time of 0.6 hour for the reboiler content, thereby minimizing reaction losses of the monomers. The reboiler was charged with the tails obtained from a similar experiment before feed was introduced to the column. The liquid in the reboiler was maintained at one hundred eighty-three degrees Celsius (183° C.).

This column was operated as column 12 in FIG. 4. Ammonolysis product having seventeen percent (17%) hexamethylene diamine ("HMD"), nineteen percent (19%) 6-aminocapronitrile ("ACN"), twenty-four percent (24%) caprolactam ("CL"), and seven percent (7%) adiponitrile ("AND"), and also high and low boiling materials (high and low boilers) was kept stirred and blanketed in nitrogen in a feed tank under a pressure of seven to eight (7 to 8) psig. Before being drawn into the distillation column by pressure difference, the feed stream passed through a ninety micrometer (90 μm) filter and then an electric preheater in which it was heated to sixty degrees Celsius (60° C.). The feed flow rate was controlled automatically with a flow control valve with the signal from a mass flowmeter at 1.2 kg/h to maintain a column pressure drop of fifteen (15) torr.

The results are summarized in the Table 4–1.

TABLE 4-1

|     | Recovery, % of feed | Reaction and Physical loss/gain, % of feed | Composition % Feed | Composition % Distillate | Composition % Tails |
| --- | --- | --- | --- | --- | --- |
| HMD | 97 | Lost 3 | 17 | 40 | 0.094 |
| ACN | 95 | Lost 5 | 19 | 44 | 0.155 |
| CL  | 100 | 0 | 24 | 0.008 | 44 |
| ADN | 96 | Lost 4 | 7 | 0.015 | 13 |

Column 4.2 The distillation column used as Column 2.2 in Example 2, described above, was operated as column 15 in FIG. 4. A tails stream from the first column containing forty-one percent (41%) caprolactam ("CL") and seventeen percent (17%) adiponitrile ("AND") and high boiling materials was fed into the column, after passing through ninety micrometer (90 μm) filter. The reboiler described in Example 2, Column 2.2 was also used.

To prevent the various streams from freezing the lines leading to the distillate receiver and the cold traps were kept at eighty degrees Celsius (80° C.) by electric heating tapes and the tails line was heated using high pressure steam to about one hundred thirty (130° C.).

The results are summarized in the Table 4–2.

TABLE 4-2

|     | Recovery, % of feed | Reaction and Physical loss/gain, % of feed | Composition % Feed | Composition % Distillate | Composition % Tails |
| --- | --- | --- | --- | --- | --- |
| CL  | 100 | 0 | 41 | 63 | 0.166 |
| ADN | 101 | Gained 1 | 17 | 27 | 0.271 |

Column 4.3 Column 36 in FIG. 4 was the same as Column 2.3 in Example 2.

Discussion The advantages of separations shown in FIGS. 2, 3 and 4 over the prior art shown in FIG. 1 can be seen in the lower Reaction and Physical Losses and higher recoveries of the individual distillation steps. The tables in Comparative Example 1 and Examples 2, 3 and 4 show the results for the individual distillation steps.

One can also calculate the overall recovery of useful monomers by mathematically combining the experimental results of the individual steps. The calculated overall recovery of the monomers in the Comparative Example 1 is sixty seven percent (67%). In contrast, the overall recovery calculated for the separation shown in FIG. 3 is ninety-five percent (95%) and the overall recovery calculated for the separation shown in FIG. 4 is ninety-six percent (96%).

An experiment to exemplify column 18 in FIG. 2 was not performed. However, if the monomer recoveries for this column were assumed to be ninety-five percent (95%) then the overall recovery for the separation shown in FIG. 2 can be calculated to be ninety-one percent (91%).

Those skilled in the art, having the benefit of the teachings of the present invention, may impart numerous modifications thereto. These modifications are to be construed as lying within the contemplation of the present invention, as defined by the appended claims.

What is claimed is:

1. A process for separating into fractions an output stream from an ammonolysis reactor, the output stream containing at least three useful reaction products, at least one useful reaction product being a first monomer having an amine functionality with a first predetermined vapor pressure associated therewith, at least one other useful reaction product being a high boiling polyamide intermediate material having a vapor pressure lower than the first predetermined vapor pressure, and at least one other useful reaction product being a first reactive monomer having a vapor pressure intermediate the lower vapor pressure and the first predetermined vapor pressure, the process comprising the step of:

as a first treatment of the output stream that separates at least one of the useful reaction products from the others, using a first distillation column to separate the first monomer having the amine functionality and the first reactive monomer having the intermediate vapor pressure from the high boiling polyamide intermediate material.

2. The process of claim 1 wherein the first monomer having the amine functionality and the first reactive monomer having the intermediate vapor pressure are both taken as a distillate fraction from the first distillation column.

3. The process of claim 2 further comprising the step of:

(b) using a second distillation column, separating the distillate fraction from the first distillation column into a distillate fraction containing the first monomer having the amine functionality and a tails fraction containing the first reactive monomer.

4. The process of claim 3, wherein the output stream from the reactor also contains a fourth useful reaction product,
the fourth useful reaction product being a second reactive monomer having a vapor pressure intermediate the lower vapor pressure and the first predetermined vapor pressure,
the second reactive monomer separates from both the first and the second distillation columns with the first reactive monomer,
the process further comprising the step of:
using a third distillation column, separating the second reactive monomer as a distillate fraction from the first reactive monomer as a tails fraction.

5. The process of claim 4, wherein the third distillation column has a reboiler associated therewith,
wherein the first reactive monomer is taken as a tails fraction from the third distillation column,
and wherein the residence of the first reactive monomer in the reboiler of the third distillation column is less than two hours.

6. The process of claim 2, wherein the output stream from the reactor also contains a fourth useful reaction product,
the fourth useful reaction product being a second reactive monomer having a vapor pressure intermediate the lower vapor pressure and the first predetermined vapor,
the second reactive monomer separates from the first distillation column with the first reactive monomer,
the process further comprising the step of:
using a second distillation column, separating the second reactive monomer as a distillate fraction from the first reactive monomer as a tails fraction.

7. The process of claim 6, wherein the second distillation column has a reboiler associated therewith,
wherein the first reactive monomer is taken as a tails fraction from the second distillation column,
and wherein the residence of the first reactive monomer in the reboiler of the second distillation column is less than two hours.

8. The process of claim 2, wherein the output stream from the reactor also contains a fourth useful reaction product,
the fourth useful reaction product being a second monomer having an amine functionality,
the second amine monomer separates from the first and the second distillation column with the first amine monomer,
further comprising the step of:
using another distillation column separating the first amine monomer as a distillate fraction from the second amine monomer as a tails fraction.

9. The process of claim 1 wherein the first monomer having the amine functionality is taken as a distillate fraction from the first distillation column and the first reactive monomer having the intermediate vapor pressure is taken as a side draw stream from the first distillation column.

10. The process of claim 9, wherein the output stream from the reactor also contains a fourth useful reaction product,
the fourth useful reaction product being a second reactive monomer having a vapor pressure intermediate the lower vapor pressure and the first predetermined vapor,
the second reactive monomer separating from the side draw of the first distillation column with the first reactive monomer,
the process further comprising the step of:
using a second distillation column, separating the second reactive monomer as a distillate fraction from the first reactive monomer as a tails fraction.

11. The process of claim 10, wherein the second distillation column has a reboiler associated therewith,
wherein the first reactive monomer is taken as a tails fraction from the second distillation column, and
wherein the residence of the first reactive monomer in the reboiler of the second distillation column is less than two hours.

12. The process of claim 9, wherein the output stream from the reactor also contains a fourth useful reaction product,
the fourth useful reaction product being a second monomer having an amine functionality,
the second amine monomer separates from the first distillation column with the first amine monomer,
further comprising the step of:
using another distillation column, separating the first amine monomer as a distillate fraction from the second amine monomer as a tails fraction.

13. The process of claim 1 wherein the high boiling polyamide intermediate material is taken as a tails fraction from the first distillation column.

14. The process of claim 13, wherein the first distillation column has a reboiler associated therewith, and wherein the residence of the tails from the first distillation column is less than one hour.

15. The process of claim 1, wherein the output stream from the reactor also contains a volatile material having a vapor pressure higher than the first predetermined vapor pressure,
wherein at least the first monomer having the amine functionality is taken as a distillate fraction from the first distillation column, and
wherein the volatile material separates from the first distillation column in a distillate stream with the first monomer having the amine functionality,
further comprising the step of:
(b) using another distillation column, separating the distillate stream from the first distillation column into a distillate fraction containing the volatile material having a vapor pressure higher than the first predetermined vapor pressure and a tails fraction containing the first monomer having the amine functionality.

16. A process for separating into fractions an output stream from an ammonolysis reactor, the output stream containing at least three useful reaction products,
at least one useful reaction product being a first monomer having an amine functionality with a first predetermined vapor pressure associated therewith,
at least one other useful reaction product being a high boiling polyamide intermediate having a vapor pressure lower than the first predetermined vapor pressure, and
at least one other useful reaction product being a first reactive monomer having a vapor pressure intermediate the lower vapor pressure and the first predetermined vapor pressure,
the process comprising the steps of:
(a) as a first treatment of the output stream that separates at least one of the useful reaction products from the others, using a first distillation column to separate the first monomer having the amine functionality from the first reactive monomer having the intermediate vapor pressure and the high boiling polyamide intermediate material; and (b) immediately following step (a), using a second distillation column to separate the first reactive monomer having the intermediate vapor pressure from the high boiling polyamide intermediate material.

17. The process of claim 16, wherein the output stream from the reactor also contains a fourth useful reaction product, the fourth useful reaction product being a second monomer having an amine functionality, the second amine monomer separates from the first distillation column with the first amine monomer, further comprising the step of:

(b) using another a second distillation column, separating the first amine monomer as a distillate fraction from the second amine monomer as a tails fraction.

18. The process of claim 16, wherein the output stream from the reactor also contains a fourth useful reaction product, the fourth useful reaction product being a second reactive monomer having a vapor pressure intermediate the lower vapor pressure and the first predetermined vapor, the second reactive monomer separating from the second distillation column with the first reactive monomer, the process further comprising the step of:

using a third distillation column, separating the second reactive monomer as a distillate fraction from the first reactive monomer as a tails fraction.

19. The process of claim 16, wherein the output stream from the reactor also contains a volatile material having a vapor pressure higher than the first predetermined vapor pressure, wherein at least the first monomer having the amine functionality is taken as a distillate fraction from the first distillation column, and wherein the volatile material separates from the first distillation column in the distillate fraction stream with the first monomer having the amine functionality, the method further comprising the step of:

using another distillation column, separating the distillate fraction from the first distillation column into a distillate fraction containing the volatile material having a vapor pressure higher than the first predetermined vapor pressure and a tails fraction containing the first monomer having the amine functionality.

20. The process of claim 16, wherein the first distillation column has a reboiler associated therewith, and wherein the residence of the tails from the first distillation column is less than one hour.

* * * * *